United States Patent [19]

Kesling, Jr.

[11] 4,239,904
[45] Dec. 16, 1980

[54] PROCESS FOR THE PREPARATION OF URETHANES

[75] Inventor: Haven S. Kesling, Jr., Drexel Hill, Pa.

[73] Assignee: Atlantic Richfield Company, Los Angeles, Calif.

[21] Appl. No.: 45,882

[22] Filed: Jun. 6, 1979

Related U.S. Application Data

[63] Continuation-in-part of Ser. No. 882,520, Mar. 1, 1978, abandoned, which is a continuation of Ser. No. 754,150, Dec. 27, 1976, abandoned.

[51] Int. Cl.$^3$ ........................................... C07C 125/065
[52] U.S. Cl. ................................. 560/157; 260/455 R; 260/465.5 R; 560/115; 560/132; 560/134; 560/152; 560/156; 560/160; 560/161; 560/162; 560/163; 560/165; 560/167
[58] Field of Search ............... 560/157, 115, 132, 134, 560/162, 152, 156, 160, 161, 163, 165, 167; 260/455 R, 465.5 R

[56] References Cited

FOREIGN PATENT DOCUMENTS 1105866 12/1961 Fed. Rep. of Germany ........... 560/159
94613 6/1960 Netherlands .............................. 560/157

OTHER PUBLICATIONS

Saegusa et al., Bull. Chem. Soc., Japan, vol. 42, pp. 2610–2614, 1969.
B. Nefedor et al., Izc. Akad. Nauk. S.S.S.R., Ser Khim, No. 7, pp. 1536–1540, 1973.
Saegusa et al., Tetrahedron Letters, vol. 49, pp. 6125–6129, 1966.

*Primary Examiner*—Natalie Trousof
*Assistant Examiner*—G. T. Breitenstein
*Attorney, Agent, or Firm*—Coleman R. Reap

[57] ABSTRACT

A process for the preparation of urethanes by reacting a tertiary amine, an alcohol and carbon monoxide in the presence of a catalytic quantity of a copper salt, oxygen and a dehydrating agent is disclosed. The reaction is preferably carried out using a copper halide catalyst and dehydrating agents which combine with water to release the alcohol used in the preparation of the urethane product.

16 Claims, No Drawings

PROCESS FOR THE PREPARATION OF URETHANES

RELATED APPLICATIONS

This is a continuation-in-part application of U.S. patent application Ser. No. 882,520 filed Mar. 1, 1978, now abandoned which in turn is a continuation application of U.S. patent application Ser. No. 754,150 filed Dec. 27, 1976, now abandoned.

BACKGROUND OF THE INVENTION

This invention relates to the preparation of urethanes and, more particularly, to the preparation of urethanes by reaction between tertiary amines, alcohols, and carbon monoxide.

Urethanes have many important industrial and medical uses, including the preparation of drugs, such as tranquilizers and muscle relaxants, the production of herbicides and insecticides, and the preparation of isocyanates which are important building blocks for the production of polyurethanes.

Increasing interest in urethanes has led to investigations for more economical and efficient processes for their production. Recent research has been directed to the preparation of urethanes by the carbonylation reaction between amines, alcohols, and carbon monoxide using various metal catalysts. Unfortunately, these reactions have been generally catalyzed by expensive Group VIII noble metal catalysts, such as the salts of palladium and platinum. Some success has been observed in the oxidative carbonylation of primary and secondary aliphatic amines to urethanes with carbon monoxide and alcohols using relatively inexpensive copper salts.

Netherlands Pat. No. 94,613 discloses the preparation of urethanes by the reaction of amines, alcohols and carbon monoxide, preferably using copper compound catalysts. Although this patent recommends that the reaction be carried out in the absence of water, there is no teaching of the use of water removal means. Other publications suggest that the presence of water favors carbamate production in this reaction. For example, West German Pat. No. 1,105,866 which discloses the preparation of urea compounds by the carbonylation of amines with carbon monoxide using copper compounds, states that drying agents can be added to the reaction mixture to substantially eliminate the production of carbamates. Due to the fact that tertiary amines do not have an available site for carbonylation it would not be expected that they could be used for the preparation of urethanes by this process.

Since carbon monoxide is a very inexpensive starting material and copper salts are relatively inexpensive catalysts, the preparation of urethanes from tertiary amines, alcohols and carbon monoxide using copper salt catalysts is potentially of considerable economic importance. Accordingly, it would be desirable to adapt this procedure to the preparation of urethanes from tertiary amines.

SUMMARY OF THE INVENTION

The above-described process has been improved by this invention so that urethanes can now be prepared by the reaction between tertiary aliphatic or cycloaliphatic amines, alcohols and carbon monoxide using copper salts as catalysts. Accordingly, it is an object of the invention to present an improved method for the preparation of urethanes. It is another object of the invention to present a method for preparing urethanes by the reaction of carbon monoxide, tertiary alipatic or cycloaliphatic amines and alcohols. It is another object of the invention to present a method of preparing urethanes using copper salts as catalysts. It is another object of the invention to present a method for producing urethanes in high yields by the reaction of tertiary aliphatic or cycloaliphatic amines, alcohols and carbon monoxide using copper salt catalysts. It is another object of the invention to present a method of preparing urethanes from tertiary aliphatic or cycloaliphatic amines, alcohols and carbon monoxide using a regenerating copper catalyst system. These and other objects of the invention will become more obvious from the following description and examples.

The above objects are achieved by reacting the tertiary amines, alcohols and carbon monoxide using a copper salt catalyst in the presence of a small amount of oxygen or an oxygen-containing gas mixture and employing means for water removal such as incorporating dehydrating agents in the reaction mixture. The reaction is generally carried out at a temperature in the range of about 60° to 300° C. and a pressure of about 1 to 700 atmospheres. In preferred embodiments the copper salt is a copper halide, the reaction zone temperature is in the range of about 100° to 250° C., the reaction zone pressure is in the range of about 50 to 150 atmospheres, dehydrating agents which release the alcohol used as a reactant are used, and the amount of oxygen present in the reaction zone is less than the lower limit of the explosive range of mixtures of oxygen and carbon monoxide.

DESCRIPTION OF THE INVENTION

The carbonylation reaction of the invention may be carried out in any high pressure batch-type or continuous reactor. A general procedure is to charge the amine, alcohol, dehydrating agent, catalyst, and the oxygen or oxygen-containing gas mixture into the reaction vessel, introduce the proper amount of carbon monoxide gas to obtain the desired reaction pressure and then heat the mixture to and maintain it at the desired temperature for the appropriate period. The reaction can be carried out batchwise or as a continuous process and the order of addition of the reactants to the reaction vessel may be varied as desired. The reaction products can be conveniently recovered by any conventional method such as filtration, distillation, etc. to effect separation of the urethane from unreacted materials, catalyst, by-products, etc.

Any monofunctional or polyfunctional tertiary aliphatic or cycloaliphatic amine or mixture of such tertiary amines having a hydrogen atom on a carbon atom adjacent to the amine nitrogen atom can be used in the process of the invention. The amine reactant has the structural formula $R(NR_1R_2)_n$ wherein R, $R_1$ and $R_2$ are the same or different organic groups, usually containing up to 30 carbon atoms each, and n is at least 1. R, $R_1$ and $R_2$ can be the same or different aliphatic or cycloaliphatic, saturated or unsaturated groups and each group preferably contains up to 18 and most preferably up to 8 carbon atoms. R, $R_1$ and $R_2$ may be unsubstituted, i.e., comprised solely of carbon and hydrogen, or they may contain pendant or in-chain atoms other than carbon and hydrogen, such as oxygen, nitrogen, sulfur, the halogens, etc., or groups containing these atoms. Common atoms or groups containing these atoms include chlorine, bromine, hydroxy, ether, ester, mercaptan, thioether, thioester, amino, amido, nitro, nitroso, etc. When n is 1 the amine is monofunctional and when n is greater than 1 the amine is polyfunctional. Preferred amines are those in which n is 1 to 3. If it is desired, a mixture of two or more tertiary amines may be used as the amine reactant.

Representative tertiary aliphatic and cycloaliphatic amines include trimethylamine, triethylamine, tripropylamine, tributylamine, trioctylamine, dimethylethylamine, dimethyllaurylamine, methylethyloleylamine, (3-chlorobutyl)-dimethylamine, (4-hydroxybutyl)-ethylmethylamine, N,N-dimethylcyclohexylamine, methyldicyclohexylamine, (3-nitrocyclohexyl)-dimethylamine, etc.

The preferred tertiary amines are the saturated aliphatic amines in which each alkyl group contains up to 8 carbon atoms, such as trimethylamine, diethylpropylamine, etc.

The alcohol component used in the process of the invention has the structural formula $R(OH)_n$ wherein R is a mono- or polyfunctional aliphatic aromatic or cycloaliphatic organic radical usually having 1 to 20 carbon atoms, and n is at least 1. When R is aliphatic or cycloaliphatic it preferably has 1 to 12 and most preferably 1 to 8 carbon atoms. When R is aromatic it is usually comprised of 1 to 3 condensed or non-condensed rings and is preferably mononuclear. R can be unsubstituted, i.e., a hydrocarbon group, or it can contain atoms other than hydrogen or carbon in its main chain or in groups pendent from the main chain. These substituents do not substantially interfere with the reaction of the invention. Typical substituents present in alcohols useful in the invention include halogen atoms and ether, ester, amino, amido, cyano, nitro, nitroso, mercapto, thioester, carboxy, alkoxy, etc., groups. When n is 1 the alcohol is monofunctional and when n is greater than 1 the alcohol is polyfunctional. In preferred embodiments n varies from 1 to 6 and most preferably from 1 to 3.

Representative alcohols within the scope of the above description include methanol, ethanol, n-, iso-, sec- and tert-butanol, amyl alcohol, hexanol, lauryl alcohol, cetyl alcohol, allyl alcohol, oleyl alcohol, 3-chloro-heptanol, ethoxyethanol, cyclohexanol, methylcyclohexanol, cyclohexenol, phenol, benzyl alcohol, chlorobenzyl alcohol, cresol, o-nitrobenzyl alcohol, p-aminophenol, anisyl alcohol, β-naphthol, 1,4-butanediol ethylene glycol, 1,3-propanediol, 1,3,6-hexanetriol, 1,4-cyclohexanediol, etc. The preferred alcohols are the mono and difunctional saturated aliphatic or cycloaliphatic alcohols containing up to 8 carbon atoms, such as methanol, ethanol, butanol, cyclohexanol, and 1,4-butanediol, ethylene glycol and aromatic alcohols comprised of one aromatic ring, such as benzyl alcohol, phenol and 2,4-toluenediol.

The equivalents ratio of total tertiary amine to alcohol is not critical, but is usually about 0.8:1 to 2.2:1 and preferably about 0.9:1 to 1.1:1.

The copper salts usable as catalysts in the process of the invention include copper(I) and copper(II) salts and mixtures of these. In general, any copper salt usable as a catalyst can be used in the invention. The copper salt anions may be inorganic, such as the halides, sulfates, sulfites, nitrates, nitrites, carbonates, etc.; or organic, such as acyl groups, including acetate, formate, propionate, alkoxides such as methoxide, ethoxide, etc.

Examples of representative copper salts are copper(I) chloride, copper(II) chloride, copper(II) bromide, copper(I) iodide, copper(II) formate, copper(II) acetate, copper(I) propionate, copper(II) methoxide, copper(I) ethoxide, etc. The preferred copper salts are the halides, particularly the copper(II) halides, such as copper(II) chloride and copper(II) bromide.

The amount of catalyst used in the reaction may vary from the minimum amount which is catalytically effective up to about 15%, based on the total weight of tertiary amine present in the reaction zone. Amounts greater than about 15% can be used, if desired, however, the efficiency of the reaction decreases as larger amounts of catalyst are employed. The amount of copper salt catalyst usually used in the process of the invention varies from about 0.01 to about 15%, and preferably from about 0.1 to about 5%, based on the total weight of tertiary amine present in the reaction zone.

A ligand or coordination complex compound of the metal catalyst can be included, if desired, in the catalyst formulation to modify the properties of the copper salt catalyst. Examples of suitable compounds include organic ligands, such as alkyl or aryl phosphines and phosphine oxides, arsines or stibines, heterocyclic amines, such as pyridine, and inorganic ligands, such as tin chloride, etc. When these agents are included they are often used in amounts up to about four molar equivalents of ligand per mole of copper.

The reaction is carried out in the presence of a catalyst oxidizing agent. During the reaction between the carbon monoxide and the tertiary amine, the copper(II) ions are reduced to copper(I) ions. The oxidizing agent functions to oxidize the copper(I) back to the copper(II) state. It is not known what additional part the oxidizing agent plays in the process of the invention, but it has been discovered that tertiary amines will not react with carbon monoxide to produce urethanes in the absence of an oxidizing agent, such as oxygen. Suitable oxidizing agents include oxygen or other suitable oxidizing agents, such as quinone. When oxygen is used it may be introduced as pure oxygen or as a component in a gas mixture, such as air. The amount of oxygen present in the reaction zone at any given time is preferably such that the concentration of oxygen is less than 6.1 volume percent. This is the lower limit of the explosive range of oxygen in carbon monoxide as determined from the tables on pages 1771-1772 of the Handbook of Chemistry and Physics, 37th Edition 1955. Although the reaction can be carried out at oxygen levels of 6.1 volume percent or greater, it is preferred to keep the oxygen and carbon monoxide levels at safe concentrations to avoid the hazard of an explosion.

During the course of the reaction between the tertiary amine, alcohol and carbon monoxide reoxidation of copper(I) to copper(II) produces water as a by-product. Although water can be tolerated when aliphatic urethanes are prepared by the reaction used in this invention, it has been discovered that tertiary amine-containing groups will not react with alcohols and carbon monoxide to produce urethanes unless the reaction is carried out under conditions such that the water formed during the reaction process is removed from the reaction zone. In the present invention this is accomplished by the use of process techniques, such as azeotropic distillation or by carrying out the reaction in the presence of dehydrating agents. When azeotropic distillation is employed the water can be removed with a portion of the alcohol or other solvent. Suitable azeotropic mixtures are those formed between alcohols and water. It is preferable to use dehydrating agents in the process of the invention. Especially preferred dehydrating agents are those which react chemically with water to release alcohols as exemplified by the following reactions:

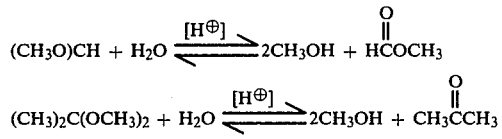

Suitable dehydrating agents include orthoesters, ketals, acetals, enolethers, trialkylorthoborates. Preferred dehydrating agents are those which will release lower alcohols, i.e., alipatic or cycloaliphatic alcohols having up to 8 carbon atoms in their structures, upon reaction with water. Particularly suitable dehydrating agents are those which, upon contact with water, release the particular alcohol from which the urethane is being prepared. Examples of preferred dehydrating agents are trimethylorthoformate, triethylorthoformate, tributylorthoformate, 2,2-dimethoxypropane, 2,2-di-n-butoxypropane, 1,1-dimethoxycyclohexane, 1,1-di-n-butoxycyclohexane, 1,1-dimethoxymethane, 1,1-diethoxyethane, 2-ethoxyprop-2-ene, 1-methoxycyclohex-1-ene, trimethylborate. The most preferred dehydrating agents are the orthoesters and ketals which react with water to release alcohols having up to 6 carbon atoms in their structures, It is most preferred that the alcohol being released be the alcohol which is used as the reactant.

The reaction can be carried out with or without a solvent. However, it is preferred to use a solvent. When lower molecular weight amines and excess alcohol are reacted there is no need for additional solvents. However, in some cases, for example when higher molecular weight reactants are used it may be desirable to conduct the reaction in the presence of a solvent. Preferred solvents are the non-oxidizable polar solvents, such as methyl acetate, chlorobenzene, etc. It is usually preferred to use a sufficient quantity of solvent to completely dissolve the reactants and to prevent localized overheating. The optimum amounts for each reaction system can be easily determined.

The following examples illustrate specific embodiments of the invention. Unless otherwise indicated parts and percentages are on a weight basis.

EXAMPLE I

A solution of 6.275 g (62.5 mmole) triethylamine, 26.53 g (250 mmole) trimethylorthoformate, and 90 ml of absolute methanol are charged into a 300 ml stainless steel stirred autoclave along with 0.84 g (6.25 mmole) anhydrous copper(II) chloride. The autoclave is sealed and charged with carbon monoxide to a pressure of 1000 psig. The temperature in the autoclave is raised to and maintained at 150° C. The reaction is initiated by charging oxygen into the autoclave until the pressure reaches 1050 psig. A pressure drop of 75-150 psi over the course of 15 minutes is observed. The oxygen cycle is repeated six times over the course of two hours. A total pressure drop of 525 psi is observed. GLC (gas-liquid chromatograph) analysis indicates that 6.405 g (48.9 mmole) N,N-diethylmethylcarbamate is formed. Based on triethylamine as a limiting reagent, a selectivity of 95 mole % to N,N-diethylmethylcarbamate at 92% triethylamine conversion is obtained.

EXAMPLE II

A solution of 6.275 g (62.50 mmole) triethylamine, 26.53 g (250 mmole) trimethylorthoformate and 90 ml of absolute methanol is charged into the autoclave described in Example I, along with 0.7140 g copper(I) iodide (3.75 mmole) and 0.9518 g (3.75 mmole). The reaction temperature is 150° C. and the total initial carbon monoxide pressure is 1000 psig. The reaction is initiated by charging oxygen into the autoclave until the pressure reaches 1050 psig. A total pressure drop of 225 psi is observed over the course of a two-hour period. GLC analysis shows that the product contains N,N-diethylmethylcarbamate.

EXAMPLE III

A solution of 26.53 g (250 mmole) trimethylorthoformate and 90 ml of absolute methanol is charged into the autoclave described in Example I, along with 0.84 g copper(II) chloride (6.25 mmole). After the autoclave is sealed, 3.695 g (62.5 mmole) trimethylamine is charged into the autoclave. The reaction temperature is 125° C. and the total initial system pressure is adjusted to 1000 psig with carbon monoxide. The reaction is initiated by charging oxygen into the autoclave until the pressure reaches 1050 psig. A total pressure drop of 490 psi is observed over the course of a two hour residence period. The liquid product contains 3.99 g N,N-dimethylmethylcarbamate (5.05 mmole) according to GLC analysis. Based on trimethylamine as a limiting reagent a selectivity of 84 mole % to N,N-dimethylmethylcarbamate at 96% trimethylamine conversion is observed.

EXAMPLE IV

A solution of 11.585 g (62.5 mmole) tributylamine, 26.53 g (250 mmole) trimethylorthoformate and 90 ml of absolute methanol is charged into the autoclave described in Example I along with 0.84 g copper(II) chloride (6.25 mmole). The reaction temperature is 125° C. and the total initial carbon monoxide pressure was 1000 psig. The reaction is initiated by charging oxygen into the autoclave until the pressure reaches 1050 psig. A total pressure drop of 568 psi is observed over the course of a two hour residence period. The liquid product contains 10.1925 g N,N-dibutylmethylcarbamate (54.5 mmole) according to GLC analysis. Based on tributylamine as a limiting reagent, a selectivity of 90.5 mole % to N,N-dibutylmethylcarbamate at 96.4% tributylamine conversion is observed.

EXAMPLE V

A solution of 6.2750 g (62.5 mmole) triethylamine, 80.74 g cyclohexanone di-n-butyl ketal (250 mmole, 70.6 wt. % cyclohexanone di-n-butylketal and 8.4 wt.% cyclohexanone) and 70 ml of 1-butanol are charged into the autoclave described in Example I, along with 0.84 g copper(II) chloride (62.5 mmole). The reaction temperature is 150° C. and the total initial carbon monoxide pressure is 1000 psig. (50 psi incremental additions of oxygen are used). A total pressure drop of 490 psi is observed over the course of a two hour residence period. The liquid product contains 9.1250 g N,N-diethylbutylcarbamate (52.75 mmole) according to GLC analysis. Based on triethylamine as a limiting reagent, a selectivity of 87.9 mole % to N,N-diethylbutylcarbamate at 96% triethylamine conversion is observed.

EXAMPLE VI

A solution of 6.2750 g (62.5 mmole) triethylamine, 26.04 g (250 mmole) 2,2-dimethoxypropane and 90 ml of absolute methanol are charged into the autoclave described in Example I, along with 0.84 g copper(II) chloride (6.25 mmole). The reaction temperature is 150° C. and the total initial carbon monoxide pressure was 1000 psig (50 psi incremental additions of oxygen are used). A total pressure drop of 470 psi is observed over the course of a two hour residence period. The liquid product contains 6.3525 g N,N-diethylmethylcarbamate (48.5 mmole) according to GLC analysis. Based on triethylamine as a limiting reagent, a selectivity of 82.2 mole % to N,N-diethylmethylcarbamate at 94.4% triethylamine conversion is observed.

EXAMPLE VII

A solution of 6.2750 g (62.5 mmole) triethylamine, 30.00 g molecular sieve 4 A° and 90 ml of absolute methanol is charged into the autoclave described in Example I, along with 0.84 g copper(II) chloride (6.25 mmole). The reaction temperature is 150° C. and the total initial carbon monoxide pressure is 1000 psig. (50 psi incremental addition of oxygen are used). A total pressure drop of 430 psi is observed over the course of a two hour residence period. The liquid product contains 6.06 g N,N-diethylmethylcarbamate (46.25 mmole) according to GLC analysis. Based on triethylamine as a limiting reagent a selectivity of 77.7 mole % to N,N-diethylmethylcarbamate at 95.2% triethylamine conversion is observed.

EXAMPLE VIII

A solution of 6.275 g (62.5 mmole) triethylamine, 6.25 mmole triethylammonium sulfate prepared "in -situ" from 0.6275 g triethylamine and 0.2950 g sulfuric acid (concentrated), 26.53 g (250 mmole) trimethylorthoformate and 90 ml of absolute methanol is charged into the autoclave described in Example I, along with 0.84 g anhydrous copper(II) chloride (6.25 mmole). The reaction temperature is 60° C. and the total initial carbon monoxide pressure was 1000 psig. Oxygen is charged into the autoclave in increments of 50 psi. A total pressure drop of 360 psi is observed over a two hour period. GLC analysis indicates that N,N-diethylmethylcarbamate is formed. The triethylammonium sulfate aids in the reoxidation of copper(I) back to copper(II) and increases the rate of reaction at low reaction temperatures.

Although the invention has been described with particular reference to specific examples, it is understood that the scope of the invention is not limited thereto but is only determined by the breadth of the appended claims.

I claim:

1. A process for the preparation of urethanes which comprises reacting, at a temperature of about 60° to 300° C. and a pressure of about 1 to 700 atmospheres a tertiary aliphatic or cycloaliphatic amine, an alcohol and carbon monoxide in the presence of a salt selected from copper I salts, copper II salts and mixtures of these, oxygen or an oxygen-containing gas mixture present in an amount less than the minimum amount necessary to form an explosive mixture of carbon monoxide and oxygen and a dehydrating agent.

2. The process of claim 1 wherein the copper salt is present in an amount of about 0.01 to 15% based on the total weight of amine present.

3. The process of claim 2 wherein the copper compound is an inorganic salt.

4. The process of claim 3 wherein the copper salt is a copper halide.

5. The process of claim 4 wherein the copper halide is present in an amount of about 0.1 to 5% based on the total weight of amine present.

6. The process of claim 4 wherein the copper halide is copper chloride.

7. The process of claim 1 wherein the dehydrating agent releases an alcohol upon hydrolysis with water.

8. The process of claim 7 wherein the alcohol released by the dehydrating agent is the same as the alcohol used as reactant.

9. The process of claim 8 wherein the dehydrating agent is a member of the group consisting of orthoesters, ketals, acetals, enolethers, trialkylorthoborates, and mixtures of these.

10. The process of claim 1 wherein an organic non-oxidizable polar solvent is present in the reaction zone.

11. A process for the preparation of urethanes which comprises reacting, at a temperature of about 60° to 300° C. and a pressure of about 1 to 700 atmospheres a tertiary aliphatic or cycloaliphatic amine, an alcohol and carbon monoxide in the presence of about 0.01 to 15%, based on the total weight of amine present, of a copper halide catalyst selected from copper I halide, copper II halide and mixtures of these, oxygen in an amount less than the minimum amount necessary to form an explosive mixture of carbon monoxide and oxygen, and an organic dehydrating agent selected from the group consisting of orthoesters, ketals, acetals, enolethers and orthoborates which, when hydrolyzed with water, release the same alcohol that is used as a reactant.

12. The process of claim 11 wherein the copper halide catalyst is copper chloride or copper bromide or mixtures of these and it is present in an amount of about 0.1 to 5%, based on the total weight of amine present.

13. The process of claim 12 wherein the alcohol is selected from aliphatic alcohols having 1 to 8 carbon atoms, cycloaliphatic alcohols having up to 8 carbon atoms and aromatic alcohols comprised of 1 aromatic ring.

14. The process of claim 13 wherein said dehydrating agent is an orthoester or a ketal.

15. The process of claim 13 wherein the alcohol is methanol, ethanol, propanol, or butanol.

16. The process of claim 11 wherein said tertiary amine is a trialkylamine.

* * * * *